United States Patent [19]

Camden et al.

[11] 4,233,235

[45] Nov. 11, 1980

[54] METHOD FOR MAKING DIPEROXYACIDS

[75] Inventors: James B. Camden, Germantown, Tenn.; Mark L. McCarty, Loveland, Ohio

[73] Assignee: The Procter & Gamble Company, Cincinnati, Ohio

[21] Appl. No.: 15,393

[22] Filed: Feb. 26, 1979

Related U.S. Application Data

[63] Continuation-in-part of Ser. No. 895,411, Apr. 11, 1978, abandoned, which is a continuation-in-part of Ser. No. 829,310, Mar. 31, 1977, abandoned.

[51] Int. Cl.$^3$ .................. C07C 179/10; C07C 179/15
[52] U.S. Cl. .................................................. 260/502 R
[58] Field of Search ........................ 260/502 R, 502 A

[56] References Cited

U.S. PATENT DOCUMENTS

| | | | |
|---|---|---|---|
| 2,314,385 | 3/1943 | Bludworth | 260/502 R |
| 2,806,045 | 9/1957 | Gross | 260/502 R |
| 2,813,885 | 11/1957 | Swern et al. | 260/502 R |
| 2,813,896 | 11/1957 | Krim | 260/502 R |
| 2,814,641 | 11/1957 | Phillips et al. | 260/502 R |
| 2,816,147 | 12/1957 | Weber et al. | 260/502 R |
| 3,079,511 | 2/1963 | Silbert et al. | 260/502 R |
| 3,140,312 | 7/1964 | Kurhajec et al. | 260/502 R |
| 3,235,584 | 2/1966 | Blumbergs | 260/502 R |
| 3,284,491 | 11/1966 | Korach | 260/502 R |
| 4,087,455 | 5/1978 | Prescher et al. | 260/502 R |
| 4,119,660 | 10/1978 | Hutchins | 260/502 R |
| 4,147,720 | 4/1979 | Berkowitz | 260/502 R |

FOREIGN PATENT DOCUMENTS

| | | | |
|---|---|---|---|
| 864135 | 8/1978 | Belgium | 260/502 R |
| 865205 | 9/1978 | Belgium | 260/502 R |
| 635620 | 1/1962 | Canada | 260/502 R |
| 744391 | 10/1966 | Canada | 260/502 R |

OTHER PUBLICATIONS

Palermo et al. "Crystallization from Solutions and Metals, Chem. Engr. Progress Symposium Ser. 95", vol. 65:34–43, (1969).
Parker et al. "Peroxides. IV. Aliphatic Diperacids" J. Amer. Chem. Soc., vol. 79, pp. 1929–1931, (1957).

*Primary Examiner*—Werren B. Lone
*Attorney, Agent, or Firm*—Ronald L. Hemingway; Richard C. Witte

[57] ABSTRACT

A continuous process for making aliphatic diperoxyacids comprising continuously adding a dibasic acid having from about 8 to about 16 carbon atoms, sulfuric acid, hydrogen peroxide and water to a continuous stirred reactor. The diperoxyacid formed is continuously withdrawn from the reactor.

10 Claims, No Drawings

METHOD FOR MAKING DIPEROXYACIDS

CROSS-REFERENCE TO RELATED APPLICATIONS

This application is a continuation-in-part of application Ser. No. 895,411, entitled "Method for Making Diperoxyacids", filed Apr. 11, 1978, now abandoned, which in turn is a continuation-in-part of application Ser. No. 829,310, entitled "Method for Making Diperoxyacids", filed Aug. 31, 1977, now abandoned.

BACKGROUND OF THE INVENTION

The present invention is related to an improved method for making aliphatic diperoxyacids having from about 8 to about 16 carbon atoms, preferably from 11 to about 16 carbon atoms, and most preferably 12 carbon atoms.

Peroxygen bleaching agents in general and peroxyacid compounds in particular have long been recognized as effective bleaching agents for use when the adverse color and fabric damage effects of harsh halogen active bleaching agents cannot be tolerated. See, for example, Canadian Pat. No. 632,620, Jan. 30, 1962, to McCune. This attractive nature of peroxyacid compounds (particularly diperoxydodecanedioic acid) makes it desirable to be able to make them in the most economical manner.

The prior art teaches the making of peroxyacid compounds in several ways. Parker et al. in *Journal American Chemical Society*, 79, 1929 (1957), disclose making diperoxyacids by dissolving a dibasic acid in sulfuric acid and adding hydrogen peroxide dropwise. U.S. Pat. No. 3,079,411, Feb. 26, 1963, to Silbert et al., discloses forming long chain aliphatic peroxyacids by combining an aliphatic acid with an alkanesulfonic acid and then treating the combination with an excess of hydrogen peroxide. U.S. Pat. No. 2,813,896, Nov. 19, 1957, to Krimm, discloses forming peroxyacids by combining sulfuric acid and hydrogen peroxide and subsequently treating the combination with a carboxylic acid. The reaction is conducted so that there is at least one mole of sulfuric acid present at the end of the reaction for every six moles of water. All of the above disclosed methods utilize the batch manufacturing approach.

The use of continuous processes for making diperoxyacids has also been disclosed. See, for example, U.S. Pat. No. 3,235,584, Feb. 15, 1966, to Blumbergs wherein it is disclosed to react an organic acid halide with an alkali metal or alkaline earth metal peroxide to form a salt of a peroxycarboxylic acid. Also U.S. Pat. No. 3,284,491, Nov. 8, 1966, to Korach et al. wherein a peroxyacid is formed in a single liquid phase.

While the prior art teaches several methods for making peroxyacids, it does not suggest the advantages for using a continuous stirred reactor for making peroxyacids of the type disclosed herein utilizing the sulfuric acid, water, hydrogen peroxide reaction medium. The present inventors have discovered that a continuous reactor can produce aliphatic diperoxyacids having significantly larger crystals than those formed from a batch process. This allows for the crystals to be collected more easily and economically due to increased filtration rates.

It is therefore an object of the present invention to provide a method for making diperoxyacids which have increased crystal size.

This and other objects of the present invention will become apparent from the following description.

All percentages and ratios used herein are by weight unless otherwise specified.

SUMMARY OF THE INVENTION

The present invention relates to a process for making aliphatic diperoxyacids comprising continuously adding a dibasic acid having from about 8 to about 16 carbon atoms (preferably from 11 to about 16 carbon atoms, and most preferably 12 carbon atoms), sulfuric acid, hydrogen peroxide and water to a stirred reactor. The diperoxyacid formed is continuously withdrawn from the reactor to maintain a constant residence time for the reactants in the reactor.

DETAILED DESCRIPTION OF THE INVENTION

The process of the present invention involves continuously adding an aliphatic, dibasic acid having from about 8 to about 16 carbon atoms, sulfuric acid, hydrogen peroxide and water to a stirred reactor. The dibasic acid is peroxidized to the diperoxyacid in the reactor which peroxyacid then precipitates in crystalline form. The crystalline product is continuously withdrawn from the reactor to maintain a constant average residence time for the reactants. The actual average residence time can be established by controlling the reactant feed rates and product withdrawal rate. It is therefore possible to vary the average residence time from several minutes to several hours depending on the actual design of the reactor. For reasons of efficiency the residence time preferably should be sufficient to allow for at least 80% conversion of the dibasic acid to the diperoxyacid.

The composition of the liquid, excluding diacids and diperoxyacids, in the reactor is important in the formation of the diperoxyacid. In the present invention it has been found that the maintained liquid composition in the reactor preferably comprises from about 60% to about 80% sulfuric acid, from about 0.5% to about 15% hydrogen peroxide and from about 5% to about 39.5% water. Most preferably, this liquid composition maintained in the reactor is from about 60% to about 80% sulfuric acid, from about 2% to about 15% hydrogen peroxide and from about 5% to about 38% water.

The ingredients used in the process of the present invention are all available in commerce. Hydrogen peroxide can be of any concentration, but is preferably from about 35% to about 70%, while sulfuric acid is preferably used in a concentration of from about 92% to about 98%. The percentages of these materials in the reaction mixture described above are based on pure materials.

The acids suitable for use herein are those aliphatic dibasic carboxylic acids having from about 8 to about 16 carbon atoms. The unsubstituted acids have the following general formula:

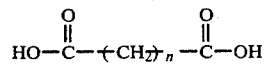

Wherein n may be an integer from about 6 to about 14. Preferred dibasic acids according to the above formula for use herein have "n" values between 9 and about 14, and particular species for use herein are 1, 11 undecanedioic acid; 1,12 dodecanedioic acid; 1, 13 tridecanedioic acid; 1, 14 tetradecanedioic acid; 1, 15 pentadecanedioic acid; and 1, 16 hexadecanedioic acid. The most preferred species is 1, 12 dodecanedioic acid.

The diperoxyacid formation reaction is as follows:

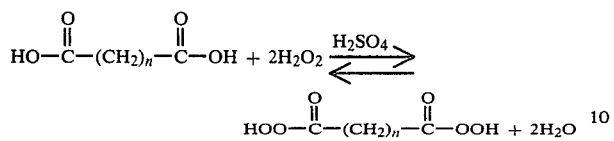

It is seen that for each mole of dibasic acid used two moles of hydrogen peroxide are required to form the diperoxyacid. It is preferred, however, that an excess of hydrogen peroxide be used in amounts ranging up to 5 times the stoichiometric required amount.

The addition of the dibasic acid to the reactor can be done in either of two distinct ways. In the first way the dibasic acid is added separately from the other reactants. In the second, preferred way, the dibasic acid is dissolved in the sulfuric acid with the solution being added via one inlet stream while aqueous hydrogen peroxide is added as a second inlet stream.

The size of the equipment required for the present process is easily determined by the skilled artisan when it has been determined that a particular production rate is desired. The material of construction is not critical but is preferably selected from the group consisting of glass, Teflon ®, stainless steel, tantalum, aluminum and porcelain.

The present process can take the form of any continuous stirred reactor. Two common forms of such reactors involve the use of a stirred tank or a high speed recycle reactor wherein the mixing is the result of the action of a pump. In the latter system the reactant streams are fed into a pump rather than into a mixing tank, the diperoxyacid product is withdrawn from the pump and run into a heat exchanger and part of the cooled product is recycled to the pump. Each system has certain advantages and may in fact be used together to obtain the benefits of both.

The preferred method of operating is the use of a reaction vessel, interconnected to an external heat exchanger. The reaction mixture is pumped and returned to the reactor. A low shear rate pump is preferred for recirculating this stream. Dibasic acid, dissolved in sulfuric acid, is added to the reaction system at the discharge of this pump. This recycle stream with sulfuric acid and dibasic acid ingredients is cooled through the heat exchanger before returning to the reaction vessel. Diperoxyacid product is removed from the reaction vessel and then filtered to yield large solid crystals. Hydrogen peroxide is then added to the filtrate and the resulting mixture is pumped through a heat exchanger where it is cooled. After cooling, the filtrate, enriched with hydrogen peroxide, is returned to the reaction vessel.

Regardless of the particular process selected the temperature maintained in the reactor is a critical element in determining the rate and characteristics of the peroxidation reaction. In the present invention it is preferred to operate the reactor in the range of about 15° to about 45° C.

Another element which plays an important role in the reaction process is the mixing which takes place in the reactor. It is desirable in a stirred tank reactor, for maximum crystal size, to use low-shear mixing such as that provided by a slowly moving paddle type agitator. High shear, such as that supplied by a high speed radial turbine, results in the crystals being reduced in size. The selection of a pumping system in the high speed recycle process should also be made so that crystal break up is minimized.

The cooling necessary to achieve the desired temperature in either the stirred tank reactor or the recycle process can be obtained in any convenient way. For example, with the stirred tank cooling coils or a jacket in contact with the tank surface may be employed while in the recycle process a conventional tube and shell heat exchanger may be used.

As was indicated above, the different types of continuous stirred reactors may be combined. Similarly the reactor system may have included in it a portion of a plug flow reactor. Such a combination allows for improved mixing within the reactor, as well as helps to control particle size. See, for example, Becker, G. W. and Larson, M. A., "Mixing Effects in Continuous Crystallization," *Chemical Engineering Progress Symposium Series—Crystallization from Solutions and Melts,* Vol. 65. The entire volume being incorporated herein by reference.

Once the diperoxyacid product is removed from the reactor system it must be filtered and washed. The choice of an appropriate filter is dependent on the production rate desired, as well as the crystal characteristics. As with the parts of the reactor system, the skilled artisan, knowing these facts, can easily select an appropriate filter.

The peroxyacids made using the process of the present invention can be dried using conventional drying techniques with usual safeguards for handling peroxyacids being observed.

The continuous stirred tank reactor as described above, when it is started up, is charged with some of the diperoxyacid reaction product. After the reactor is operational a recycle stream may be used to supply part of the reactant liquids.

In addition to providing larger crystals, the continuous process herein can utilize faster reaction conditions with fewer safety problems than is possible with a batch reactor.

Compositions Containing the Peroxyacid Compounds

The peroxyacid compounds made using the process of the present invention can be used in a wide variety of compositions. A preferred use of the peroxyacids, particularly 1, 12 diperoxydodecanedioic acid, is as fabric bleaching agents. To insure that compositions containing the peroxyacid compounds are safe and effective, certain additives are desirably present.

It is well documented in the peroxyacid literature that peroxyacids are susceptible to a number of different stability problems, as well as being likely to cause some problems. Looking at the latter first, peroxyacids decompose exothermally and when the material is in dry granular form the heat generated must be controlled to make the product safe. The best exotherm control agents are those which are capable of liberating moisture at a temperature slighty below the decomposition temperature of the peroxyacid employed. U.S. Pat. No. 3,770,816, Nov. 6, 1973, to Nielsen, incorporated herein by reference, discloses a wide variety of hydrated materials which can serve as suitable exotherm control agents. Included among such materials are magnesium sulfate .7H$_2$O, magnesium formate dihydrate, calcium sulfate ($CaSO_4 \cdot 2H_2O$), calcium lactate hydrate, calcium sodium sulfate ($CaSO_4 \cdot 2Na_2SO_4 \cdot 2H_2O$), and hydrated forms of such things as sodium aluminum sulfate, potassium aluminum sulfate, ammonium aluminum sulfate and aluminum sulfate. Preferred hydrates are the alkali metal aluminum sulfates, particularly preferred is potassium aluminum sulfate. Other preferred exotherm control agents are those materials which lose water as the result of chemical decomposition such as boric acid, maleic acid and maleic acid. The exotherm control agent is preferably used in an amount of from about 100% to about 200% based on the weight of the peroxyacid compound.

The other problems faced when peroxyacid compounds are used fall into the area of maintaining good bleach effectiveness. It has been recognized that metal ions are capable of serving as catalyzing agents in the degradation of the peroxyacid compounds. To overcome this problem chelating agents can be used in an amount ranging from 0.005% to about 1.00% based on the weight of the composition to tie up heavy metal ions. U.S. Pat. No. 3,442,937, May 6, 1969, to Sennewald et al., discloses a chelating system comprising quinoline or a salt thereof, an alkali metal polyphosphate and, optionally, a synergistic amount of urea. U.S. Pat. No. 2,838,459, June 10, 1958, to Sprout, Jr., discloses a variety of polyphosphates as stabilizing agents for peroxide baths. These materials are useful herein as stabilizing aids. U.S. Pat. No. 3,192,255, June 29, 1965, to Cann, discloses the use of quinaldic acid to stabilize percarboxylic acids. This material, as well as picolinic acid and dipicolinic acid, would also be useful in the compositions of the present invention. A preferred chelating system for the present invention is a mixture of 8-hydroxyquinoline and an acid polyphosphate, preferably acid sodium pyrophosphate. The latter can be a mixture of phosphoric acid and sodium pyrophosphate wherein the ratio of the former to the latter is from about 0.5:1 to about 2:1 and the ratio of the mixture to 8-hydroxyquinoline is from about 1:1 to about 5:1.

In addition to the above-mentioned chelating systems to tie up heavy metals in the peroxyacid compositions, coating materials may also be used to extend the shelf life of dry granular compositions. Such coating materials may be, in general, acids, esters, ethers and hydrocarbons and include such things as wide varieties of fatty acids, derivatives of fatty alcohols, such as esters and ethers, derivatives of polyethyleneglycols such as esters and ethers and hydrocarbon oils and waxes. These materials aid in preventing moisture from reaching the peracid compound. Secondly, the coating material may be used to segregate the peracid compound from other agents which may be present in the composition and adversely affect the peracid's stability. When used in this manner the coating may be used on both the peracid compound and the other agent or either individually. The amount of the coating material used is generally from about 2.5% to about 15% based on the weight of the peroxyacid compound.

Additional agents which may be used to aid in giving good bleaching performance include such things as pH adjustment agents, bleach activators and minors such as coloring agents, dyes and perfumes. Typical pH adjustment agents are used to alter or maintain aqueous solutions of the instant compositions within the 5 to 10 pH range in which peroxyacid bleaching agents are generally most useful. Depending upon the nature of other optional composition ingredients, pH adjustments agents can be either of the acid or base type. Examples of acidic pH adjustment agents designed to compensate for the presence of other highly alkaline materials include normally solid organic and inorganic acids, acid mixtures and acid salts. Examples of such acidic pH adjustment agents include citric acid, glycolic acid, tartaric acid, gluconic acid, glutamic acid, sulfamic acid, sodium bisulfate, potassium bisulfate, ammonium bisulfate and mixtures of citric acid and lauric acid. Citric acid is preferred by virtue of its low toxicity and hardness sequestering capability.

Optional alkaline pH adjustment agents include the conventional alkaline buffering agents. Examples of such buffering agents include such salts as carbonates, bicarbonates, silicates, pyrophosphates and mixtures thereof. Sodium bicarbonate and tetrasodium pyrophosphate are highly preferred.

Optional peroxyacid bleach activators as suggested by the prior art include such materials as aldehydes and ketones. Use of these materials as bleaching activators is described more fully in U.S. Pat. No. 3,822,114, July 2, 1974, to Montgomery, incorporated herein by reference.

A preferred dry, granular bleaching product employing the peroxyacid bleach of the present invention involves combining the active peroxy compound with potassium aluminum sulfate or boric acid and the acid pyrophosphate/8-hydroxyquinoline subsequently coating this mixture with mineral oil and agglomerating the coated particles with a polyethylene glycol derivative. An alkaline pH adjustment agent is then added to the agglomerated stabilized active as a dry mix.

Optional ingredients, if utilized in combination with the active peroxyacid of the instant invention to form a complete bleaching product, comprise from about 20% to about 99% weight of the total composition. Conversely, the peroxyacid compound made using the process of the present invention comprises from about 1% to about 80% of the composition.

The bleaching compositions of the instant invention, particularly the dry granular version, can also be added to and made a part of conventional fabric laundering detergent compositions. Accordingly, optional materials for the instant bleaching compositions can include such standard detergent adjuvants as surfactants and builders. Optional surfactants are selected from the group consisting of organic anionic, nonionic, ampholytic, and zwitterionic surfactants and mixtures thereof. Optional builder materials include any of the conventional organic and inorganic builder salts including carbonates, silicates, acetates, polycarboxylates and phosphates. If the instant stabilized bleaching compositions are employed as part of a conventional fabric laundering detergent composition, the instant bleaching agent generally comprises from about 1% to about 40% by weight of such conventional detergent compositions. Conversely, the instant bleaching compositions can optionally contain from about 60% to about 99% by weight of conventional surfactant and builder materials. Further examples of suitable surfactants and builders are given below.

Water-soluble salts of the higher fatty acids, i.e., "soaps," are useful as the anionic surfactant herein. This class of surfactants includes ordinary alkali metal soaps such as the sodium, potassium, ammonium and alkanolammonium salts of higher fatty acids containing from about 8 to about 24 carbon atoms and preferably from about 10 to about 20 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soaps.

Another class of anionic surfactants includes water-soluble salts, particularly the alkali metal, ammonium and alkanolammonium salts, of organic sulfuric reaction products having in their molecular structure an alkyl group containing from about 8 to about 22 carbon atoms and a sulfonic acid or sulfuric acid ester group. (Included in the term "alkyl" is the alkyl portion of acyl groups.) Examples of this group of synthetic surfactants which can be used in the present detergent compositions are the sodium and potassium alkyl sulfates, especially those obtained by sulfating the higher alcohols ($C_8$–$C_{18}$ carbon atoms) produced by reducing the glycerides of tallow or coconut oil; and sodium and potassium alkyl benzene sulfonates, in which the alkyl group contains from about 9 to about 15 carbon atoms in straight chain or branched chain configuration, e.g., those of the type described in U.S. Pat. Nos. 2,220,099, and 2,477,383, incorporated herein by reference.

Other anionic surfactant compounds useful herein include the sodium alkyl glyceryl ether sulfonates, especially those ethers or higher alcohols derived from tallow and coconut oil; sodium coconut oil fatty acid monoglyceride sulfonates and sulfates; and sodium or potassium salts of alkyl phenol ethylene oxide ether sulfate containing about 1 to about 10 units of ethylene oxide per molecule and wherein the alkyl groups contain about 8 to about 12 carbon atoms.

Other useful anionic surfactants herein include the water-soluble salts of esters of $\alpha$-sulfonated fatty acids containing from about 6 to 20 carbon atoms in the ester group; water-soluble salts of 2-acyloxy-alkane-1-sulfonic acids containing from about 2 to 9 carbon atoms in the acyl group and from about 9 to about 23 carbon atoms in the alkane moiety; alkyl ether sulfates containing from about 10 to 20 carbon atoms in the alkyl group and from about 1 to 30 moles of ethylene oxide; water-soluble salts of olefin sulfonates containing from about 12 to 24 carbon atoms; and $\beta$-alkyloxy alkane sulfonates containing from about 1 to 3 carbon atoms in the alkyl group and from about 8 to 20 carbon atoms in the alkane moiety.

Preferred water-soluble anionic organic surfactants herein include linear alkyl benzene sulfonates containing from about 11 to 14 carbon atoms in the alkyl group; the tallow range alkyl sulfates; the coconut range alkyl glyceryl sulfonates; and alkyl ether sulfates wherein the alkyl moiety contains from about 14 to 18 carbon atoms and wherein the average degree of ethoxylation varies between 1 and 6.

Specific preferred anionic surfactants for use herein include: sodium linear $C_{10}$–$C_{12}$ alkyl benzene sulfonate; triethanolamine $C_{10}$–$C_{12}$ alkyl benzene sulfonate; sodium tallow alkyl sulfate; sodium coconut alkyl glyceryl ether sulfonate; and the sodium salt of a sulfated condensation product of tallow alcohol with from about 3 to about 10 moles of ethylene oxide.

It is to be recognized that any of the foregoing anionic surfactants can be used separately herein or as mixtures.

Nonionic surfactants include the water-soluble ethoxylates of $C_{10}$–$C_{20}$ aliphatic alcohols and $C_6$–$C_{12}$ alkyl phenols. Many nonionic surfactants are especially suitable for use as suds controlling agents in combination with anionic surfactants of the type disclosed herein.

Semi-polar surfactants useful herein include water-soluble amine oxides containing one alkyl moiety of from about 10 to 28 carbon atoms and 2 moieties selected from the group consisting of alkyl groups and hydroxyalkyl groups containing from 1 to about 3 carbon atoms; water-soluble phosphine oxides containing one alkyl moiety of about 10 to 28 carbon atoms and 2 moieties selected from the group consisting of alkyl groups and hydroxyalkyl groups containing from about 1 to 3 carbon atoms; and water-soluble sulfoxides containing one alkyl moiety of from about 10 to 28 carbon atoms and a moiety selected from the group consisting of alkyl and hydroxyalkyl moieties of from 1 to 3 carbon atoms.

Ampholytic surfactants include derivaties of aliphatic or aliphatic derivatives of heterocyclic secondary and tertiary amines in which the aliphatic moiety can be straight chain or branched and wherein one of the aliphatic substituents contains from about 8 to 18 carbon atoms and at least one aliphatic substituent contains an anionic water-solubilizing group.

Zwitterionic surfactants include derivatives of aliphatic quaternary ammonium, phosphonium and sulfonium compounds in which the aliphatic moieties can be straight or branched chain, and wherein one of the aliphatic substituents contains from about 8 to 18 carbon atoms and one contains an anionic water-solubilizing group.

The instant granular compositions can also comprise those detergency builders commonly taught for use in laundry compositions. Useful builders herein include any of the conventional inorganic and organic water-soluble builder salts, as well as various water-insoluble and so-called "seeded" builders.

Inorganic detergency builders useful herein include, for example, water-soluble salts of phosphates, pyrophosphates, orthophosphates, polyphosphates, phosphonates, carbonates, bicarbonates, borates and silicates. Specific examples of inorganic phosphate builders include sodium and potassium tripolyphosphates, phosphates, and hexametaphosphates. The polyphosphonates specifically include, for example, the sodium and potassium salts of ethylene diphosphonic acid, the sodium and potassium salts of ethane 1-hydroxy-1,1-diphosphonic acid, and the sodium and potassium salts of ethane-1,1,2-triphosphonic acid. Examples of these and other phosphorus builder compounds are disclosed in U.S. Pat. Nos. 3,159,581; 3,213,030; 3,422,021; 3,422,137; 3,400,176 and 3,400,148, incorporated herein by reference. Sodium tripolyphosphate is an especially preferred, water-soluble inorganic builder herein.

Non-phosphorus containing sequestrants can also be selected for use herein as detergency builders. Specific examples of non-phosphorus, inorganic builder ingredients include water-soluble inorganic carbonate, bicarbonate, borate and silicate salts. The alkali metal, e.g., sodium and potassium, carbonates, bicarbonates, borates (Borax) and silicates are particularly useful herein.

Water-soluble, organic builders are also useful herein. For example, the alkali metal, ammonium and substituted ammonium polyacetates, carboxylates, polycarboxylates, succinates, and polyhydroxysulfonates are useful builders in the present compositions and processes. Specific examples of the polyacetate and polycarboxylate builder salts include sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred non-phosphorous builder materials (both organic and inorganic) herein include sodium carbonate, sodium bicarbonate, sodium silicate, sodium citrate, sodium oxydisuccinate, sodium mellitate, sodium nitrilotriacetate, and sodium ethylenediaminetetraacetate, and mixtures thereof.

Another type of detergency builder material useful in the present compositions and processes comprises a water-soluble material capable of forming a water-insoluble reaction product with water hardness cations in combination with a crystallization seed which is capable of providing growth sites for said reaction product.

Specific example of materials capable of forming the water-insoluble reaction product include the water-soluble salts of carbonates, bicarbonates, sequicarbonates, silicates, aluminates and oxalates. The alkali metal, especially sodium, salts of the foregoing materials are preferred for convenience and economy.

Another type of builder useful herein includes various substantially water-insoluble materials which are capable of reducing the hardness content of laundering liquors, e.g., by ion-exchange processes. Examples of such builder materials include the phosphorylated cloths disclosed in U.S. Pat. No. 3,424,545, Bauman, issued Jan. 28, 1969, incorporated herein by reference.

The complex aluminosilicates, i.e., zeolite-type materials, are useful presoaking/washing adjuvants herein in that these materials soften water, i.e., remove $Ca^{++}$ hardness. Both the naturally occurring and synthetic "zeolites", especially zeolite A and hydrated zeolite A materials, are useful for this builder/softener purpose. A description of zeolite materials and a method of preparation appears in Milton, U.S. Pat. No. 2,882,243, issued Apr. 14, 1959, incorporated herein by reference.

Composition Preparation

The bleaching compositions of the instant invention are prepared in any conventional manner such as by admixing ingredients, by agglomeration, by compaction or by granulation in the case of the dry granule form. In one method for preparing such compositions, a peroxyacid-water mixture containing from about 50% by weight to about 80% by weight of water is combined in proper proportions with any optional components to be utilized within the bleaching granules themselves. Such a combination of ingredients is then thoroughly mixed and subsequently run through an extruder. Extrudate in the form of noodles is then fed into a spheronizer (also known by the trade name, Marumerizer) to form approximately spherical particles from the peroxyacid-containing noodles. The bleaching granules can then be dried to the appropriate water content. Upon leaving the spheronizer, such particles are screened to provide uniform particle size.

Bleaching granules prepared in this manner can then be admixed with other granules of optional bleaching or detergent composition materials. Actual particle size of either the bleach-containing granules or optional granules of additional material is not critical. If, however, compositions are to be realized having commercially acceptable flow properties, certain granule size limitations are highly preferred. In general, all granules of the instant compositions preferably range in size from about 100 microns to 3000 microns, more preferably from about 100 microns to 1300 microns.

Additionally, flowability is enhanced if particles of the present invention are of approximately the same size. Therefore, preferably the ratio of the average particle sizes of the bleach-containing granules and optional granules of other materials varies between 0.5:1 and 2.0:1.

Bleaching compositions of the present invention are utilized by dissolving them in water in an amount sufficient to provide from about 1.0 ppm to 100 ppm available oxygen in solution. Generally, this amounts to about 0.01% to 0.2% by weight of composition in solution. Fabrics to be bleached are then contacted with such aqueous bleaching solutions.

The process of the instant invention is illustrated by the following example:

EXAMPLE I

The advantage for the continuous process of the present invention over a batch process is demonstrated in the experiment described below.

A. Diperoxydodecanedioic acid is made using a batch reactor equipped with a stirrer wherein (a) 50 grams of dodecanedioic acid is dissolved in 213.6 grams of 97% sulfuric acid with the solution being cooled to 10° C.; (b) a hydrogen peroxide mixture is prepared by mixing together, while keeping the temperature under 27° C., 116.7 grams of 67.8% hydrogen peroxide, 57.5 grams of water and 213.3 grams of 97% sulfuric acid; (c) the mixture of (b) is cooled to 6° C.; and (d) the solution of (a) and the mixture of (b) are mixed together quickly and the mixture is maintained at a temperature of 35° C. for a period of one hour. The diperoxydodecanedioic acid formed precipitates and the precipitate is washed with water and collected by means of filtration. The collected crystals are evaluated for particle size, filtration rate and available oxygen.

B. A second batch of diperoxydodecanedioic acid which is seeded is made using a batch reactor equipped with a stirrer wherein (a) and (b) as described above are duplicated. To the peroxide mixture (b) are added 200 grams of the reaction product from A at a temperature of about 9° C. with the final mixture temperature going to about 30° C. To this mixture is added the dodecanedioic acid/sulfuric acid solution as described in (a) above and the temperature of the reaction mix is maintained at about 35° C. for one hour. The diperoxyacid formed is filtered, washed with water and analyzed for particle size, filtration rate and available oxygen.

C. A continuous stirred tank reaction is carried out by continuously feeding to a reactor similar to the batch reactors the following two streams: (a) 16.3 g/min. of a solution containing 10.4% dodecanedioic acid and 89.6% sulfuric acid (97%); and (b) 5.94 g/min. of a mixture containing 45.2% hydrogen peroxide and 54.8% water. The reactor temperature is increased from 20° C. to about 35° C. during the first 90 minutes and is maintained at about 35° C. for another 210 minutes. The diperoxyacid product is continuously withdrawn from the reactor vessel, filtered, washed and analyzed. The rate of product removal is such that the average residence time in the reactor is about 56 minutes. The reactor vessel at the start of the reaction is filled with reaction product which has been formed using a batch reactor as in A above.

The increase in crystal size for the continuous reactor is shown in the following table.

COMPARISON OF BATCH AND CONTINUOUS REACTIONS

|  | Continuous | Batch Unseeded | Batch Seeded |
|---|---|---|---|
| Reaction Temperature, °C. | 35 | 35 | 35 |
| Premix Concentration* |  |  |  |
| Sulfuric acid | 68.9 | 68.9 | 68.9 |
| Hydrogen Peroxide | 13.1 | 13.1 | 13.1 |
| Water | 18.0 | 18.0 | 18.0 |
| Reaction Time, Minutes | 56 (average residence time) | 60 | 60 |
| Product analysis |  |  |  |
| Final available oxygen level, % | 11.4 | 11.4 | 11.2 |
| Average crystal size, micron | 47 | 14 | 19 |
| Filtration rate, g filtrate/min. cm². of filter cake thickness | 6.2 | 0.26 | 1.1 |

*Concentration of the liquid phase (excluding the dodecanedioic acid) entering the reactor prior to reaction.

It is seen that the continuous process yields larger, more easily filtered, crystals than either a conventional batch reaction or a batch reaction which has been seeded with diperoxyacid.

Results similar to those given above are obtained when the dibasic acid is another acid selected from the group consisting of acids having the structure

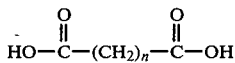

where n is a number from about 6 to about 14, preferably 9 to about 14, and most preferably 10.

What is claimed is:

1. A continuous process for making diperoxyacids of the formula

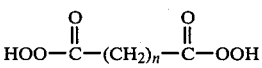

wherein n is from about 6 to about 14, said diperoxyacids having a crystalline form and an average crystal size substantially greater than about 19 microns, comprising:

(a) continuously adding to a stirred reactor of temperature from about 15° C. to about 45° C. the following materials:
(1) hydrogen peroxide;
(2) water;
(3) sulfuric acid; and
(4) a dibasic acid of the formula

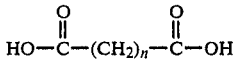

wherein n is from about 6 to about 14;
(b) continuously withdrawing from the reactor diperoxyacid product formed as a result of the oxidation of the dibasic acid;
(c) filtering the diperoxyacid product; and
(d) washing the diperoxyacid product with water and drying it;

wherein the inlet flow rates to the reactor of sulfuric acid, hydrogen peroxide and water are sufficient to maintain a liquid concentration of about 60% to about 80% sulfuric acid, about 0.5% to about 15% hydrogen peroxide, and about 5% to about 39.5% water in the reactor.

2. A process according to claim 1 wherein the inlet flow rates of sulfuric acid, hydrogen peroxide and water are sufficient to maintain a liquid concentration of about 60% to about 80% sulfuric acid, about 2% to about 15% hydrogen peroxide and about 5% to about 38% water in the reactor.

3. A process according to claim 2 wherein the aliphatic dibasic acid is dissolved in the sulfuric acid prior to being added to the reactor.

4. A process according to claim 3 wherein the aliphatic dibasic acid is dodecanedioic acid.

5. A process according to claim 2 wherein the reactor is a high speed, recycle reactor.

6. A process according to claim 2 where the reactor is a mixed reactor having both a stirred tank section and a high speed, recycle section.

7. A process according to claim 2 where the reactor is a mixed reactor having both a stirred tank section and a plug fow section.

8. A process according to claim 2 where the reactor is a mixed reactor having both a high speed, recycle section and a plug flow section.

9. A process according to claim 2 where the reactor is a mixed reactor having a stirred tank section, a high speed, recycle section and a plug flow section.

10. A process according to claim 1 wherein n is from 9 to about 14.

* * * * *